(12) United States Patent
Riedijk

(10) Patent No.: US 9,449,212 B2
(45) Date of Patent: Sep. 20, 2016

(54) CAPACITIVE FINGERPRINT SENSOR WITH SENSING ELEMENTS COMPRISING TIMING CIRCUITRY

(71) Applicant: FINGERPRINT CARDS AB, Göteborg (SE)

(72) Inventor: Frank Robert Riedijk, Delft (NL)

(73) Assignee: FINGERPRINT CARDS AB, Göteborg (SE)

( * ) Notice: Subject to any disclaimer, the term of this patent is extended or adjusted under 35 U.S.C. 154(b) by 0 days.

(21) Appl. No.: 14/812,578

(22) Filed: Jul. 29, 2015

(65) Prior Publication Data

US 2016/0180138 A1    Jun. 23, 2016

(30) Foreign Application Priority Data

Dec. 22, 2014 (SE) .................................... 1451633-0

(51) Int. Cl.
  *G06K 9/00* (2006.01)
  *G01R 27/26* (2006.01)
  *G06F 3/0354* (2013.01)
  *G07C 9/00* (2006.01)

(52) U.S. Cl.
  CPC ......... *G06K 9/0002* (2013.01); *G01R 27/2605* (2013.01); *G06F 3/03547* (2013.01); *G07C 9/00* (2013.01)

(58) Field of Classification Search
  CPC .... G06F 3/03547; G07C 9/00; G06K 9/0002
  USPC ........... 324/658–690; 382/124; 345/173–178
  See application file for complete search history.

(56) References Cited

U.S. PATENT DOCUMENTS

| | | | | |
|---|---|---|---|---|
| 6,411,727 B1* | 6/2002 | Harkin | ................. | G06K 9/0002 340/5.83 |
| 6,681,033 B1* | 1/2004 | Yano | ........................ | G01D 5/24 382/108 |
| 7,864,992 B2 | 1/2011 | Riedijk et al. | | |
| 2001/0025532 A1* | 10/2001 | Kramer | ................ | A61B 5/1172 73/862.68 |
| 2005/0141263 A1* | 6/2005 | Umeda | ................ | G06K 9/0002 365/149 |
| 2013/0271422 A1* | 10/2013 | Hotelling | ................ | G06F 3/044 345/174 |
| 2015/0189214 A1* | 7/2015 | Kurose | .................... | H01L 25/18 250/208.1 |

\* cited by examiner

*Primary Examiner* — Jeff Natalini
(74) *Attorney, Agent, or Firm* — Remarck Law Group PLC

(57) ABSTRACT

The present invention relates to a capacitive fingerprint sensing device for sensing a fingerprint pattern of a finger, the capacitive fingerprint sensor comprising a plurality of sensing elements, each including: a protective dielectric top layer to be touched by the finger; an electrically conductive sensing structure arranged underneath the top layer; charge measuring circuitry connected to the sensing structure for sequentially transitioning between at least a first measurement state and a second measurement state to perform a measurement sequence resulting in an output signal from the charge measuring circuitry being indicative of a change of a charge carried by the sensing structure resulting from a change in a potential difference between the finger and the sensing structure; and timing circuitry connected to the charge measuring circuitry for controlling a timing of at least one of the measurement states.

25 Claims, 8 Drawing Sheets

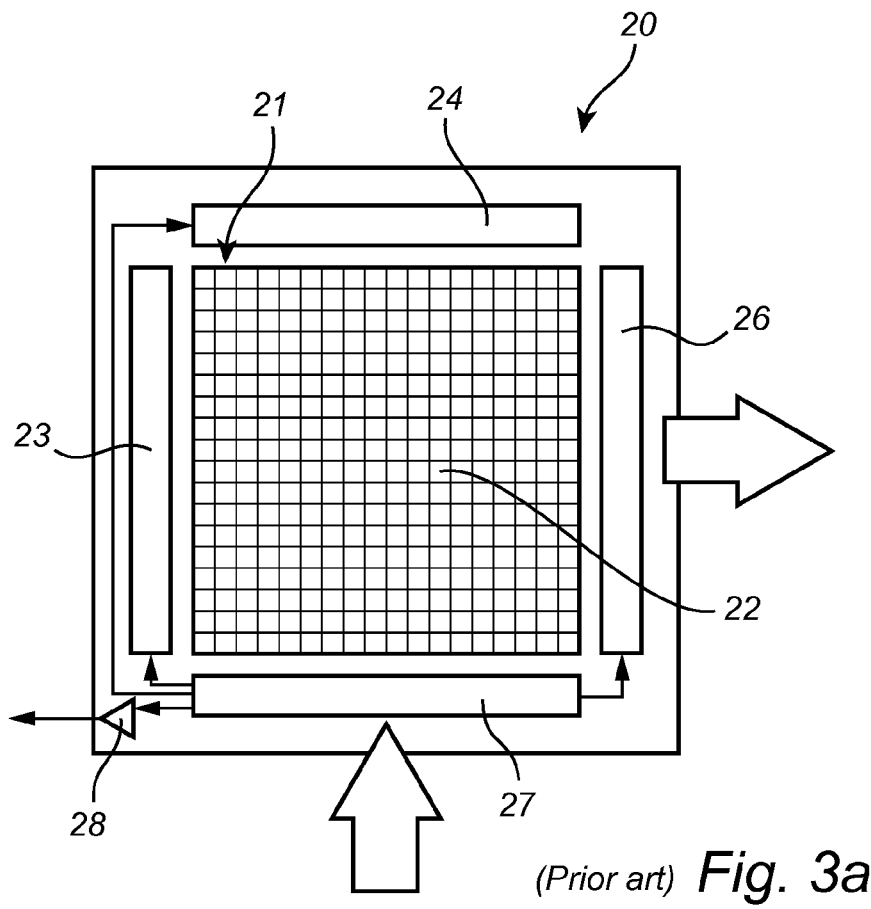
(Prior art) Fig. 3a
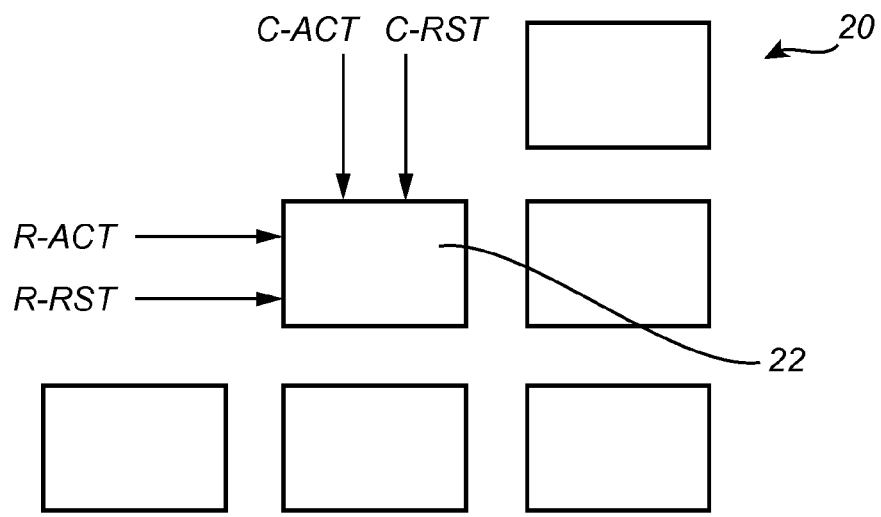
(Prior art) Fig. 3b

CAPACITIVE FINGERPRINT SENSOR WITH SENSING ELEMENTS COMPRISING TIMING CIRCUITRY

CROSS-REFERENCE TO RELATED APPLICATIONS

This application claims the benefit of Swedish Patent Application No. 1451633-0, filed Dec. 22, 2014. The disclosure of the above application is incorporated herein by reference in its entirety.

FIELD OF THE INVENTION

The present invention relates to a capacitive fingerprint sensing device and to a method of sensing a fingerprint pattern.

BACKGROUND OF THE INVENTION

Various types of biometric systems are used more and more in order to provide for increased security and/or enhanced user convenience.

In particular, fingerprint sensing systems have been adopted in, for example, consumer electronic devices, thanks to their small form factor, high performance and user acceptance.

Among the various available fingerprint sensing principles (such as capacitive, optical, thermal etc), capacitive sensing is most commonly used, in particular in applications where size and power consumption are important issues.

All capacitive fingerprint sensors provide a measure indicative of the capacitance between several sensing structures and a finger placed on or moved across the surface of the fingerprint sensor.

Some capacitive fingerprint sensors passively read out the capacitance between the sensing structures and the finger. This, however, requires a relatively large capacitance between each of sensing structure and finger. Therefore such passive capacitive sensors are typically provided with a very thin protective layer covering the sensing structures, which makes such sensors rather sensitive to scratching and/or ESD (electro-static discharge).

U.S. Pat. No. 7,864,992 discloses a fingerprint sensing system in which a driving signal is injected into the finger by pulsing a conductive structure arranged in the vicinity of the sensor array and measuring the resulting change of the charge carried by the sensing structures in the sensor array.

This type of so-called active fingerprint sensing systems generally enable measurement of the capacitance and sensing structures with a much higher signal-to-noise ratio than the above-mentioned passive systems. This, in turn, allows for a considerably thicker protective coating and thus for more robust capacitive fingerprint sensors that can be included in items subjected to considerable wear, such as mobile phones.

However, there is still room for improvement. In particular, it would be desirable to provide for fingerprint sensing through even thicker protective coatings and/or for further improved performance in respect of signal-to-noise ratio.

SUMMARY

In view of above-mentioned and other drawbacks of the prior art, it is an object of the present invention to achieve an improved capacitive fingerprint sensing device, in particular a capacitive fingerprint sensing device providing for improved sensing performance through very thick protective coatings.

According to a first aspect of the present invention, it is therefore provided a capacitive fingerprint sensing device for sensing a fingerprint pattern of a finger, the capacitive fingerprint sensor comprising a plurality of sensing elements, each including a protective dielectric top layer to be touched by the finger; an electrically conductive sensing structure arranged underneath the top layer; charge measuring circuitry connected to the sensing structure for sequentially transitioning between at least a first measurement state and a second measurement state to perform a measurement sequence resulting in an output signal from the charge measuring circuitry being indicative of a change of a charge carried by the sensing structure resulting from a change in a potential difference between the finger and the sensing structure; and timing circuitry connected to the charge measuring circuitry for controlling a timing of at least one of the measurement states.

The sensing structure may advantageously be provided in the form of a metal plate, so that a kind of parallel plate capacitor is formed by the sensing structure (the sensing plate), the local finger surface, and the protective coating (and any air that may locally exist between the local finger surface and the protective coating).

The protective coating may advantageously be at least 20 μm thick and have a high dielectric strength to protect the underlying structures of the fingerprint sensing device from wear and tear as well as ESD. Even more advantageously, the protective coating may be at least 50 μm thick. In embodiments, the protective coating may be a few hundred μm thick.

The "charge measuring circuitry" is any circuitry capable of providing an output signal that is indicative of a change of a charge carried by the sensing structure. The output signal may be analog or digital. For instance the output signal may be provided in the form of an electrical potential in relation to a reference potential. In various embodiments, the charge measuring circuitry may comprise a charge amplifier.

The charge measuring circuitry may be controllable to perform a predetermined measurement sequence involving transitioning between different measurement states in a predetermined sequence. A measurement state may be defined by a certain combination of control signals provided to the charge measuring circuitry.

It should be noted that each sensing element or group of sensing elements in the capacitive fingerprint sensing device according to embodiments of the present invention comprises timing circuitry, so that timing control of at least one of the measurement states of the charge measuring circuitry is locally controlled in each sensing element or group of sensing elements.

In other words, at least one of the point in time and the duration of at least one measurement state is locally controlled in each sensing element or group of sensing elements. It can thus be said that the timing circuitry functions as a local state machine, which may be asynchronous or synchronous, or a combination thereof.

The present invention is based upon the realization that faster operation of the sensing elements would allow multiple readouts from each sensing element, which would in turn provide for improved capacitance measurement/sensing performance, for example in terms of signal-to-noise ratio and common mode noise reduction.

The present inventor has further realized that the desired faster operation of the sensing elements can be enabled or at least greatly facilitated by providing localized timing in the sensing elements or groups of sensing elements.

By providing localized timing of at least the most time critical transition(s) between measurement states, the measurement time can be decreased and/or the design of the capacitive fingerprint sensing device facilitated. For instance, careful routing of certain timing control signals to each sensing element will not be necessary, but the timing can be initiated by an external signal selecting a particular sensing element or group of sensing elements.

It should be noted that a capacitive fingerprint sensing device may comprise a large number of sensing elements, such as in the order of at least 100 sensing elements. Some capacitive fingerprint sensing device may comprise a considerably larger number of sensing elements, such as at least 10 000 sensing elements. If the readout frequency is increased from, say, 1 MHz to, say, 20 MHz, the difference in conduction time to different sensing elements may make it difficult or even practically impossible to fulfill measurement-related timing requirements using external, central timing control.

Accordingly, embodiments of the present invention provide for a higher readout frequency, which in turn allows improved measurement performance and further enables combination of multiple output signals (sometimes referred to as a kind of filtering), whereby the common mode noise can be reduced and the signal-to-noise ratio increased.

This in turn allows for measurement through thicker coatings, such as a button or a part of the cover of an electronic device, such as a mobile phone. Furthermore, it may be possible to reduce the energy consumption of the fingerprint sensor and/or reduce the time needed to obtain a fingerprint representation (image).

According to embodiments, the timing circuitry of each sensing element may further be connected to at least one additional sensing element for additionally controlling a state of this at least one additional sensing element. For instance, the timing circuitry may control neighboring sensing elements to provide suitable voltage levels to their respective sensing structures.

According to various embodiments of the present invention, the timing circuitry may be configured to control the charge measuring circuitry to transition from the first measurement state to the second measurement state at a transition time defined by a first event and a time delay in relation to the first event.

The first event may be independently provided by the timing circuitry, or the first event may be provided by circuitry external to the sensing element.

According to various embodiments, the timing circuitry may advantageously comprise at least a first delay element having an input for receiving a first signal defining the first event and an output for providing a second signal defining a second event delayed in relation to the first event.

The first signal may be a time-varying voltage, and the first event may, for instance, be defined by a rising flank or falling flank of the first signal.

The first signal may be generated internally in the sensing element, or may, according to various embodiments be provided as a signal, which may, for example, be referred to as an activation signal, generated outside the sensing element.

The second signal may be seen as a delayed version of the first signal, but it should be understood that other transformations than a delay may have been imposed on the first signal to form the second signal. For instance, the first signal may additionally have been amplified and/or attenuated and/or inverted etc to form the second signal.

The first delay element may advantageously comprise semiconductor circuitry, such as one or more logic gates.

The second event defined by the second signal may advantageously comprise the above-mentioned transition from the first measurement state to the second measurement state.

According to various embodiments, the output of the first delay element may be coupled to the charge measuring circuitry for allowing the second signal to control operation of the charge measuring circuitry.

The output of the first delay element may be directly connected to the charge measuring circuitry, or there may be additional circuitry between the first delay element and the charge measuring circuitry. For instance, the above-mentioned second signal and an additional signal may be input to a logic gate, and the output of the logic gate may be used to control operation of the charge measuring circuitry.

Furthermore, the timing circuitry may additionally comprise a second delay element having an input coupled to the output of the first delay element and an output for providing a third signal defining a third event delayed in relation to the second event.

This third event may involve controlling the charge measuring circuitry to transition from the above-mentioned second measurement state to a third measurement state.

To that end, the output of the second delay element may be coupled to the charge measuring circuitry for allowing the third signal to control operation of the charge measuring circuitry.

According to various embodiments, moreover, the timing circuitry may further comprise at least one logic gate coupled between the output of the first delay element and the input of the second delay element. Hereby, the signal that is delayed by the second delay element may be made a logic function of the above-mentioned second signal and an additional control signal that may be generated internally in the sensing element or provided from circuitry external to the sensing element. These embodiments will thus allow conditional control of the above-mentioned second event.

Depending on the configuration of the charge measuring circuitry, the above-mentioned measurement sequence may comprise different numbers of measurement states. The timing circuitry may advantageously be adapted to the number of measurement states through the provision of a plurality of delay elements arranged in a daisy chain configuration with an output of one delay element coupled to the input of the next delay element in the sequence. The number of delay elements may be adapted to the number of measurement states, but need not directly correspond to the number of measurement states in the measurement sequence.

As an alternative or complement to using one or several delay element(s), the timing circuitry may comprise one or several feedforward and/or feedback loop(s) in combination with one or several logic gate(s). This may allow for forming physically smaller timing circuitry, which may facilitate the design of the fingerprint sensing device and/or allow for smaller sensing elements.

In embodiments, the sequence of delay elements may be a closed loop sequence which may or may not be controlled by an external signal. In embodiments, it could be advantageous to allow a sensing element to autonomously "run through" several measurement cycles before, or while, outputting a signal indicative of the capacitive coupling between the finger and the sensing structure.

In various embodiments, it may be advantageous to configure the capacitive fingerprint sensing device to allow a first sensing element or group of sensing elements to initiate the measurement sequence of a second sensing element or group of sensing elements. For instance each sensing element or group of sensing elements in row or column of the fingerprint sensing device may sequentially trigger each other to perform a measurement sequence. This will allow for a quick scan of, for example, a full column or row, which may result in a fast average signal from the full column or row. Such an average signal may be useful for, for instance, noise cancellation etc.

According to various embodiments, the above-mentioned measurement sequence may at least comprise a reset state in which a potential at an output of the charge measuring circuitry is referenced to a potential of the sensing structure.

The charge measuring circuitry may comprise a charge amplifier including a negative input connected to the sensing structure; a positive input; an output; a feedback capacitor connected between the negative input and the output; and at least one amplifier stage between the positive and negative inputs and the output, wherein the charge amplifier is configured in such a way that a potential at the negative input substantially follows a potential at the positive input.

In these embodiments, the charge measuring circuitry may further comprise reset circuitry controllable to conductively connect the negative input and the output, to discharge the feedback capacitor.

The reset circuitry may be coupled to the timing circuitry comprised in the sensing element, and the timing circuitry may control the reset circuitry to discharge the feedback capacitor, to thereby transition the charge measuring circuitry to the above-mentioned reset state.

Subsequently, the timing circuitry may control the reset circuitry to disconnect the negative input from the output, thereby allowing the feedback capacitor to hold a charge. This event will transition the charge measuring circuitry from the reset state to a measurement ready state, where the charge carried by the sensing structure can be measured using the charge amplifier.

According to embodiments, the fingerprint sensing device may further comprise excitation signal providing circuitry for providing an excitation signal exhibiting a time-varying excitation potential including recurring changes from a first potential to a second potential and back to the first potential, in relation to a potential of the finger; each of the sensing elements may further comprise demodulation circuitry connected to the charge measuring circuitry for combining the output signal from the charge measuring circuitry and a demodulation signal being timing-related to the excitation signal to provide a combined signal including a DC signal component indicating the change of the charge carried by the sensing structure; and the fingerprint sensing device may further comprise readout circuitry connected to each of the sensing elements for providing a representation of the fingerprint pattern based on the DC signal component from each of the sensing elements.

A time-varying potential should, accordingly, be understood to mean an electrical potential with a magnitude that varies over time in relation to a reference potential. The time-varying excitation potential may, for instance, be provided as a pulse train having a pulse repetition frequency or a combination of pulse repetition frequencies. The pulses in such a pulse train may, for example, be square wave pulses. Alternatively, the time-varying excitation potential may be provided as a sine wave or a combination of sine waves.

The present inventor has realized that the desired faster operation of the sensing elements can be achieved without a corresponding increase in power consumption by at least partly demodulating the sensing signal locally in the sensing element or group of sensing elements in such a way that the desired information content of the sensing signal—the above-mentioned change in charge carried by the sensing structure—is indicated by a DC signal or a near DC signal (constant voltage in relation to a reference potential of the fingerprint sensing system).

By outputting from each sensing element the change of the charge carried by the sensing structure as a DC signal component, it will not be necessary to move the readout line up and down in potential against the parasitic capacitance of the readout line, which provides for a considerably reduced energy consumption per readout event.

According to various embodiments, the capacitive fingerprint sensing device may further comprise excitation signal providing circuitry connected to the positive input and configured to change a potential at the positive input from a first potential to a second potential, to thereby change a potential of the sensing structure, thereby providing the change in potential difference between the finger and the sensing structure.

The excitation signal providing circuitry could be switching circuitry configured to switch between two or more different potentials provided on different lines. Alternatively or in combination, the excitation signal providing circuitry may comprise at least one signal source configured to provide a time-varying potential, such as a square wave voltage signal or a sine wave voltage signal.

According to embodiments, each sensing element may comprise excitation signal providing circuitry for that particular sensing element.

Furthermore, for each sensing element, the timing circuitry may be connected to the excitation signal providing circuitry for providing a first excitation control signal to the excitation signal providing circuitry for triggering the change in potential from the first potential to the second potential at a first excitation transition time; and providing a second excitation control signal to the excitation signal providing circuitry for triggering a change in potential back from the second potential to the first potential at a second excitation transition time.

According to various embodiments, the charge measuring circuitry may comprise sampling circuitry for sampling a signal indicative of a charge carried by the sensing structure at a first sampling time before the change in the potential difference between the finger and the sensing structure; and sampling the signal indicative of the charge carried by the sensing structure at a second sampling time after the change in the potential difference between the finger and the sensing structure.

The sampling circuitry may comprise first and second sampling capacitors and switching circuitry controllable to provide the above-mentioned signal indicative of the charge carried by the sensing structure to the first sampling capacitor at the first sampling time and to provide the signal to the second sampling capacitor at the second sampling time.

The procedure of sampling the sensing signal at first and second sampling times is generally referred to as correlated double sampling and removes much of the offset as well as at least low-frequency components of the common mode noise that the fingerprint sensing device may be subjected to.

The timing circuitry may advantageously be connected to the sampling circuitry for providing a first sampling control signal to the sampling circuitry for performing the sampling of the first signal at the first sampling time; and providing a second sampling control signal to the sampling circuitry for performing the sampling of the second signal at the second sampling time.

In to various embodiments the capacitive fingerprint sensing device according to the present invention may advantageously further comprise readout circuitry connected to each of the sensing elements and configured to provide a representation of the fingerprint pattern based on the output signal from each of the sensing elements.

The representation of the fingerprint pattern may be provided by the readout circuitry to other circuitry external to the capacitive fingerprint sensing device.

The capacitive fingerprint sensing device according to various embodiments of the present invention may advantageously be included in an electronic device, further comprising processing circuitry configured to: acquire the representation of the fingerprint pattern from the fingerprint sensing device; authenticate a user based on the representation; and perform at least one user-requested process only if the user is authenticated based on the representation. The electronic device may, for example, be a handheld communication device, such as a mobile phone or a tablet, a computer, or an electronic wearable item such as a watch or similar.

According to a second aspect of the present invention, there is provided a method of sensing a fingerprint pattern of a finger using a capacitive fingerprint sensor comprising a plurality of sensing elements, each including: a protective dielectric top layer to be touched by the finger; an electrically conductive sensing structure arranged underneath the top layer; and charge measuring circuitry connected to the sensing structure for sequentially transitioning between at least a first measurement state and a second measurement state to perform a measurement sequence resulting in an output signal from the charge measuring circuitry being indicative of a change of a charge carried by the sensing structure resulting from a change in a potential difference between the finger and the sensing structure, wherein the method comprises the steps of, for each of the sensing elements: providing a first signal defining a first event; delaying the first signal for providing a second signal defining a second event delayed in time in relation to the first event; and controlling the charge measuring circuitry to transition from the first measurement state to the second measurement state using the second signal as a control signal.

The step of delaying may advantageously comprise the step of passing the first signal through a delay element.

According to various embodiments, the capacitive fingerprint sensing device may comprise sampling circuitry for sampling the output signal of the charge measuring device; excitation signal providing circuitry for providing the change in potential difference between the finger and the sensing structure; and readout circuitry connected to each of the sensing elements and configured to provide a representation of the fingerprint pattern based on the output signal from each of the sensing elements, and the method may comprise the steps of providing a selection signal for selecting a sensing element; delaying the selection signal for providing a reset signal; providing the reset signal to the charge measuring circuitry for transitioning the charge measuring circuitry to a reset state; delaying the reset signal for providing a measurement ready signal; providing the measurement ready signal to the charge measuring circuitry for terminating the reset state and transitioning to a measurement ready state; delaying the measurement ready signal for providing a first sampling control signal; providing the first sampling control signal to the sampling circuitry for triggering sampling of a first signal indicative of a charge carried by the sensing structure at a first sampling time; delaying the first sampling control signal for providing a first excitation control signal; providing the first excitation control signal to the excitation signal providing circuitry for achieving the change in potential difference between the finger and the sensing structure; delaying the first excitation control signal for providing a second sampling control signal; and providing the second sampling control signal to the sampling circuitry for triggering sampling of a second signal indicative of a charge carried by the sensing structure at a second sampling time.

Further embodiments of, and effects obtained through this second aspect of the present invention are largely analogous to those described above for the first aspect of the invention.

BRIEF DESCRIPTION OF THE DRAWINGS

These and other aspects of the present invention will now be described in more detail, with reference to the appended drawings showing an example embodiment of the invention, wherein:

FIGS. 3a-b are schematic block diagrams of a fingerprint sensing device according to the prior art;

FIG. 6b schematically illustrates a timing circuit for controlling the timing of the measurement sequence performed by the charge measuring circuitry in FIG. 6a.

DETAILED DESCRIPTION OF EXAMPLE EMBODIMENTS

In the present detailed description, various embodiments of the fingerprint sensing device and method according to the present invention are mainly described with reference to a capacitive fingerprint sensing device, in which each sensing element comprises charge measuring circuitry including a charge amplifier for measuring charge carried by the sensing structure, excitation signal providing circuitry for providing an excitation or drive signal to the sensing structure and timing circuitry comprising a plurality of delay elements for controlling operation of the charge amplifier and the excitation signal providing circuitry. Moreover, the capacitive fingerprint sensing device is illustrated as a touch sensor dimensioned and configured to acquire a fingerprint representation from a stationary finger.

It should be noted that this by no means limits the scope of the present invention, which equally well includes, for example, a capacitive fingerprint sensing device including another circuit configuration for measuring the change in charge carried by the sensing structure resulting from a change in potential difference between the finger and the sensing structure. Moreover, the present invention is not limited to capacitive fingerprint sensing devices in which this change in potential difference is achieved by driving the sensing structure of the sensing element. The potential difference may instead be achieved by providing the excitation signal to the finger directly or via other sensing elements than one or several sensing element(s) presently selected for sensing. Such other sensing elements may be programmed to function as drive elements. Other sensor array configurations, such as a so-called swipe sensor (or line sensor) for acquiring a fingerprint representation from a moving finger, are also within the scope of the present invention as defined by the appended claims.

Figure 1:
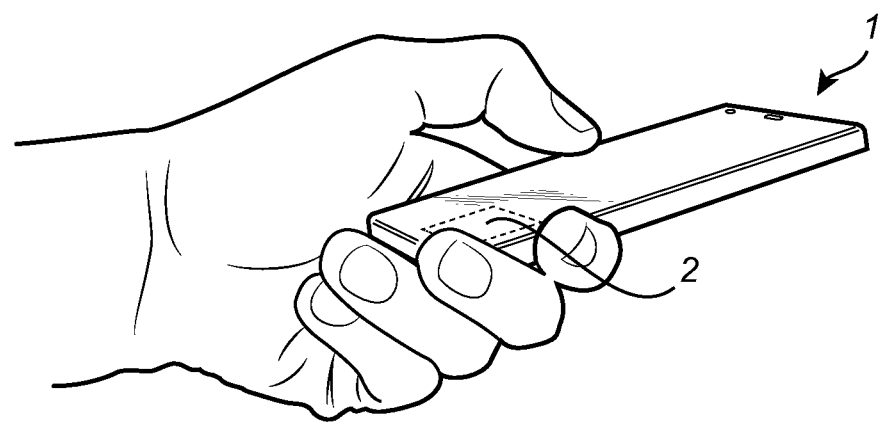
FIG. 1 schematically illustrates a mobile phone comprising a fingerprint sensing system according to an example embodiment of the present invention.

FIG. 1 schematically illustrates an application for a fingerprint sensing device according to an example embodiment of the present invention, in the form of a mobile phone 1 with an integrated fingerprint sensing device 2. The fingerprint sensing device 2 may, for example, be used for unlocking the mobile phone 1 and/or for authorizing transactions carried out using the mobile phone, etc.

Figure 2:
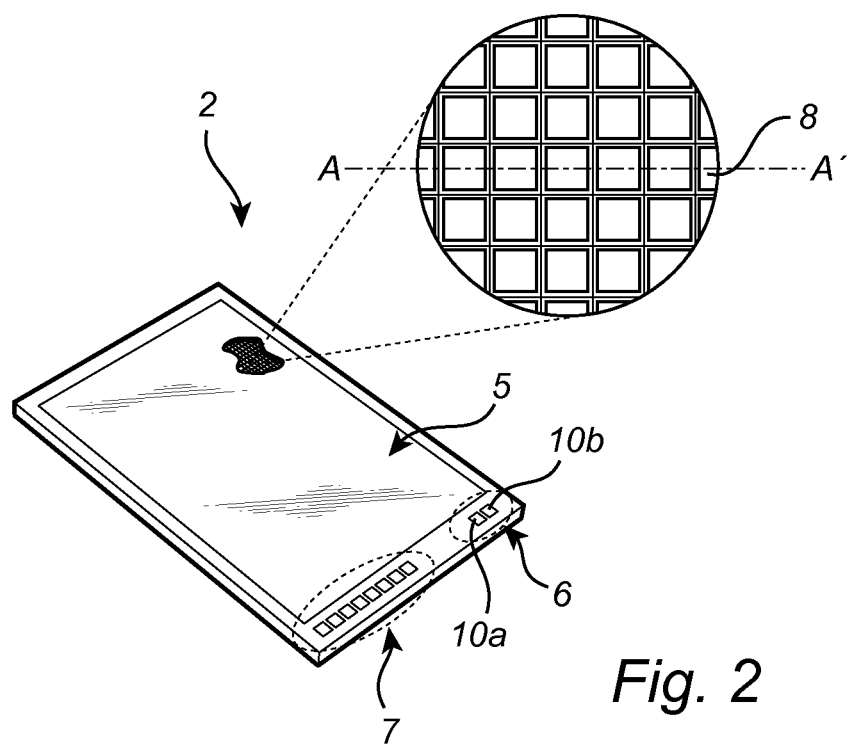
FIG. 2 schematically shows the fingerprint sensing device in FIG. 1.

FIG. 2 schematically shows the fingerprint sensing device 2 comprised in the mobile phone 1 in FIG. 1. As can be seen in FIG. 2, the fingerprint sensing device 2 comprises a sensor array 5, a power supply interface 6 and a communication interface 7. The sensor array 5 comprises a large number of sensing elements 8 (only one of the sensing elements has been indicated with a reference numeral to avoid cluttering the drawing), each being controllable to sense a distance between a sensing structure (top plate) comprised in the sensing element 8 and the surface of a finger contacting the top surface of the sensor array 5.

The power supply interface 6 comprises first 10a and second 10b contact pads, here shown as bond pads, for connection of a supply voltage $V_{supply}$ to the fingerprint sensor 2.

The communication interface 7 comprises a number of bond pads for allowing control of the fingerprint sensor 2 and for acquisition of fingerprint data from the fingerprint sensor 2.

Figure 3C:
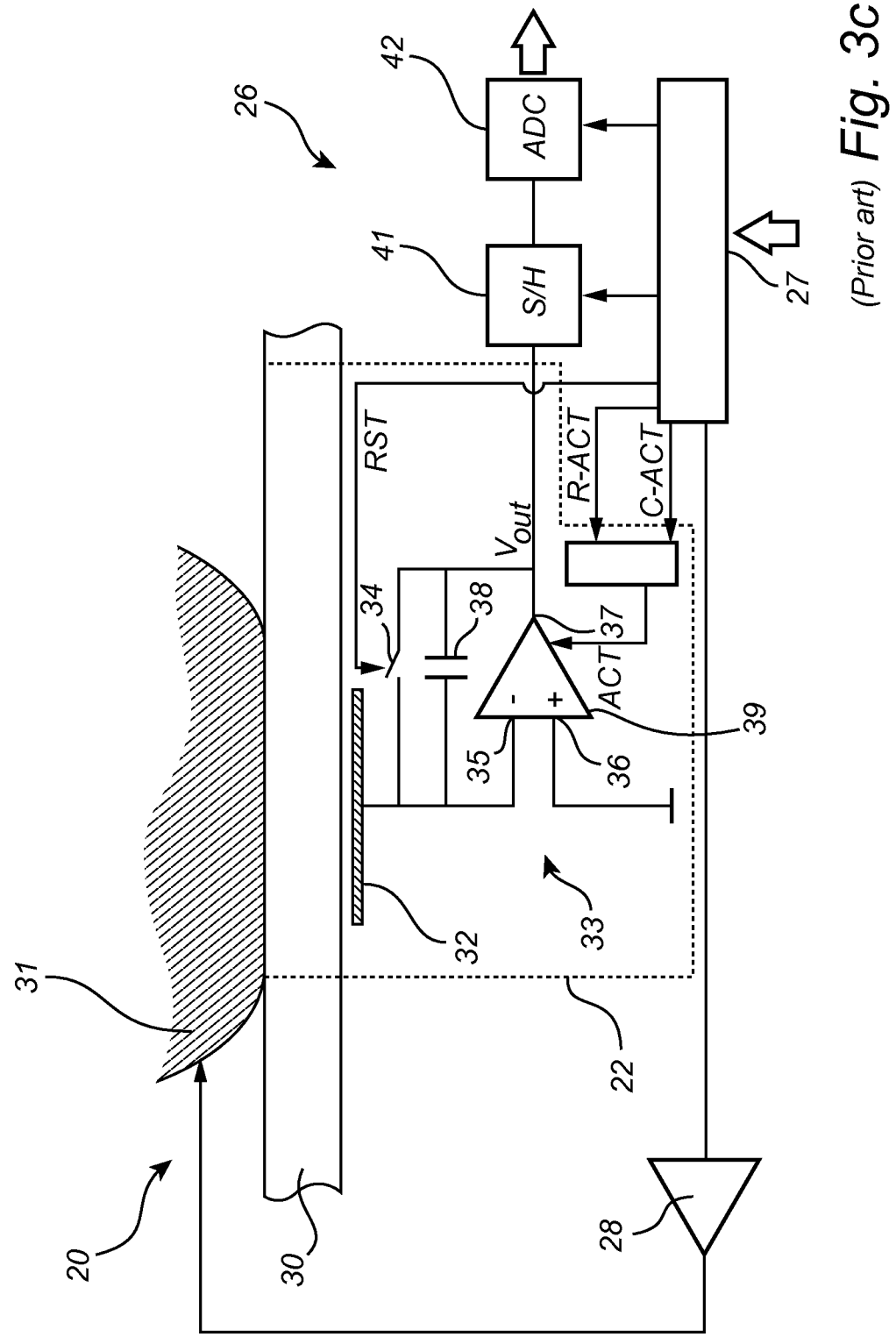
FIG. 3c is a circuit diagram schematically illustrating operation of the fingerprint sensing device in FIGS. 3a-b.

To aid the understanding of embodiments of the present invention, an example of a known capacitive fingerprint sensor will now be provided with reference to FIG. 3a-c.

FIG. 3a is a schematic block diagram of a capacitive fingerprint sensor 20 according to the prior art. Referring to FIG. 3a, the fingerprint sensor 20 comprises an array 21 of capacitive sensing elements 22, row selection circuitry 23, column selection circuitry 24, readout circuitry 26, a state machine 27 and an excitation signal amplifier 28.

The state machine 27 receives instructions, illustrated by the block arrow 29 pointing towards the state machine 27, and based on the received instructions, the state machine 27 controls the row selection circuitry 23, the column selection circuitry 24, and the readout circuitry 26. The state machine 27 also provides an excitation signal for providing drive pulses to the finger via the excitation signal amplifier 28.

After having controlled the row selection circuitry 23 and the column selection circuitry 24 to select a particular sensing element 22 as is schematically indicated in FIG. 3b, the state machine 27 also provides timing control signals to charge measuring circuitry comprised in the sensing element 22 and to the readout circuitry for reading out the sensing signal provided by the sensing element 22. In particular, the state machine 27 controls the sensing element 22 and the readout circuitry 26 to perform a measurement sequence comprising transitioning between a plurality of sequential measurement states. This will be described in greater detail below with reference to FIG. 3c, and to the exemplary timing diagram in FIG. 4.

FIG. 3c is, in part, a schematic cross-section view of one of the sensing elements 22 in the fingerprint sensing device 20 in FIG. 3a-b, and in part a functional block diagram illustrating the operation of the fingerprint sensing device 20 as controlled by the state machine 27.

Referring to FIG. 3c, the sensing element 22 comprises a protective dielectric top layer 30 to be touched by a finger 31 (FIG. 3c schematically shows a cross-section of a single ridge of a finger pattern), an electrically conductive sensing structure (plate) 32, and a charge amplifier 33. The charge amplifier 33 comprises a negative input 35, a positive input 36, an output 37, a feedback capacitor 38, and an amplifier 39.

The negative input 35 is connected to the sensing structure (plate) 32, the positive input 36 is connected to ground and the output 37 is connected to the readout circuitry 26.

The feedback capacitor 38 is connected between the negative input 35 and the output 37 and defines the amplification of the charge amplifier 33, and the sensing element 22 further comprises a reset switch 34 in parallel with the feedback capacitor 38.

Outside the sensing element 22, the block diagram in FIG. 3c schematically indicates the state machine 27, the excitation signal amplifier 28, and the readout circuitry 26 comprising a sample-and-hold circuit (S/H-circuit) 41 and an analog-to-digital converter (ADC) 42.

When the fingerprint sensing device 20 is in operation, the state machine 27 controls the timing of the charge amplifier 33 and the readout circuitry 26 as will be described below with reference to FIG. 3a-c and additionally FIG. 4.

Figure 4:
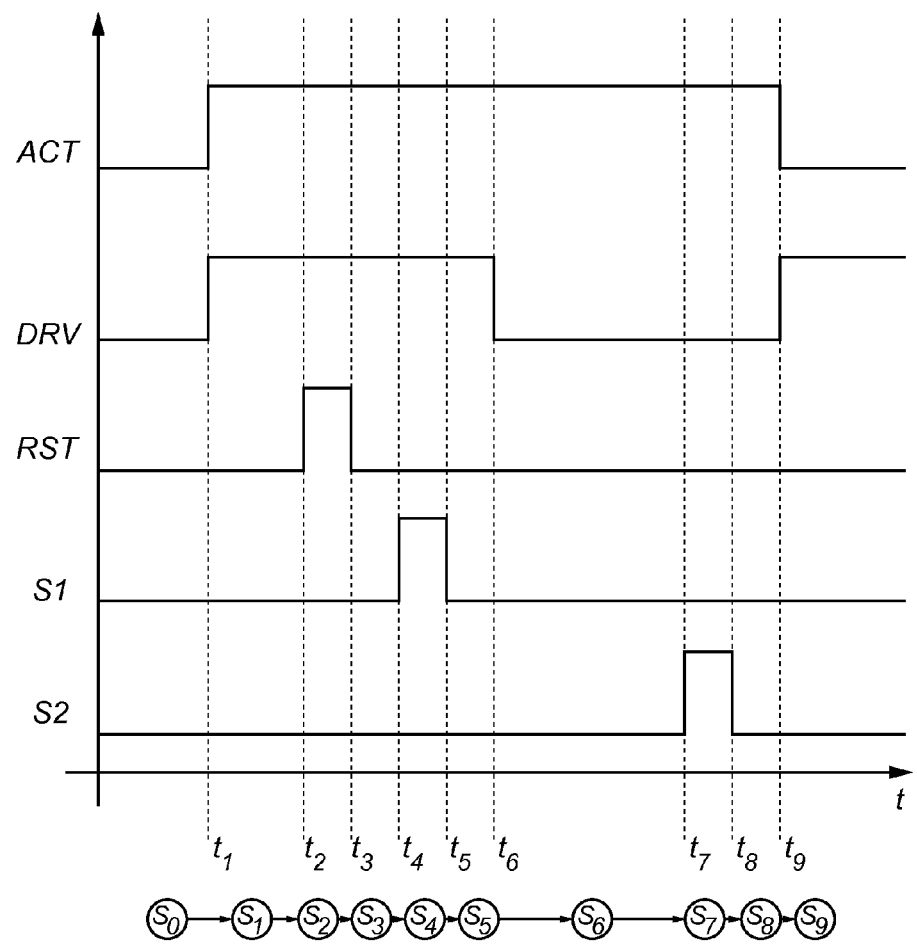
FIG. 4 is a timing diagram illustrating an exemplary measurement sequence for the capacitive fingerprint sensing device according to embodiments of the present invention, as well as for the fingerprint sensing device according to the prior art in FIG. 3c.

FIG. 4 illustrates an exemplary measurement sequence for the fingerprint sensor 20 according to the prior art, as well as for the fingerprint sensor 2 according to various embodiments of the present invention. As will be apparent through the description provided below, the main difference between the prior art fingerprint sensor 20 and the fingerprint sensor according to embodiments of the present invention is that the measurement sequence illustrated in FIG. 4, or another suitable measurement sequence, can be performed considerably faster, enabling faster readout and/or multiple readings from each sensing elements resulting in improved measurement performance.

Referring to FIG. 4, the timing diagram shown therein comprises, from top to bottom, an activation signal ACT, a drive (excitation) signal DRV, a reset signal RST, a first sampling control signal S1, and a second sampling control signal S2.

Below the timing diagram, the sequence of measurement states S0-S9 together forming the above-mentioned measurement sequence is schematically indicated.

For activation of the sensing element 22 in FIG. 3a-b, a row-selection signal and a column selection signal indicating the sensing element 22 may typically be provided. In the simplified and schematic timing diagram in FIG. 4, such selection signals are represented by a single activation signal ACT.

At a first time $t_1$, the sensing element 22 is activated by a transition of the activation signal ACT from low to high. This may, for example, involve activating the amplifier 39. At substantially the same point in time $t_1$, the drive (excitation) signal DRV provided by the state machine 27 via the excitation signal amplifier 28 to the finger 31 is controlled to go from low to high. The drive signal DRV may, for instance, be provided to the finger through galvanic connection with a finger electrode, for example a bezel (not shown) at least partly surrounding the fingerprint sensor 20. Alternatively, the drive signal DRV may be capacitively coupled to the finger 31, for example by applying the drive signal to one or several sensing elements which are presently not in a sensing state, but in a driving state.

At the time $t_1$, there is thus a transition from the "inactive" state $S_0$ to the first measurement state $S_1$ of the measurement sequence.

Application of the drive signal DRV to the finger 31 will result in a change in the charge carried by the sensing structure 32. After some time to allow the output signal from the charge amplifier to stabilize, a reset signal RST is provided at the time $t_2$ to close the reset switch 34 to thereby discharge the feedback capacitor and reference the potential at the output 37 of the charge amplifier 33 to the potential of the sensing structure (plate) 32.

Through the provision of the first flank of the reset signal, there is a transition from the first measurement state $S_1$ to the second measurement state $S_2$ (reset state).

The reset switch 34 is released (allowed to open again) at the time $t_3$, to thereby transition to the third measurement state $S_3$ (measurement ready state).

At the time $t_4$, there is a transition to the fourth measurement state $S_4$, in which the first sampling control signal $S_1$ goes from low to high to control the sample-and-hold circuit 41 to sample the sensing signal at the output 37 of the charge amplifier 33.

At the time $t_5$, there is a transition to the fifth measurement state $S_5$, in which the first sampling control signal S1 goes from high to low.

Subsequently, at the time $t_6$, the drive signal DRV goes from high to low to change the potential difference between the finger 31 and the sensing structure 32. This is also the transition to the sixth measurement state $S_6$ as is schematically indicated in FIG. 4.

At the time $t_7$, there is a transition to the seventh measurement state $S_7$, in which the second sampling control signal S2 goes from low to high to control the sample-and-hold circuit 41 to sample the sensing signal at the output 37 of the charge amplifier 33 a second time.

At the time $t_8$, there is a transition to the eighth measurement state $S_8$, in which the second sampling control signal S2 goes from high to low.

Finally, at the time $t_9$, there is a transition to the ninth measurement state $S_9$, where the sensing element 22 is deactivated and the drive signal DRV again goes from low to high. The ninth measurement state $S_9$ is identical to the initial "inactive" state $S_0$.

Although not shown in the timing diagram in FIG. 4, the measurement sequence may additionally include controlling the ADC 42 to convert the output of the S/H 41 to a digital value representing the capacitance coupling between the finger 31 and the sensing structure 32.

In the prior art fingerprint sensing system of FIG. 3a-b, the timing of the transitions between measurement states is controlled by the global state machine for each of the sensing elements 22. Due to, for example, the routing of signal lines to the sensing elements 22, the timing of state transitions may vary somewhat from sensing element to sensing element. For instance, the timing of the reset signal RST may vary between sensing elements. If there is sufficient time before the transition to the reset state $S_2$ at the second time $t_2$ and/or sufficient time after the transition from the reset state $S_2$ to the measurement ready state $S_3$ at the third time $t_3$, then the measurement will be successful. If, however, the measurement frequency in increased so that the total available time for the measurement cycle is reduced, the situation may arise that the variation in timing of the globally controlled transitions between measurement states becomes too large, so that the measurement is affected.

As will be described further below, this situation can improved, and capacitive fingerprint measurements at a higher measurement frequency are provided for through embodiments of the present invention.

Figure 5A:
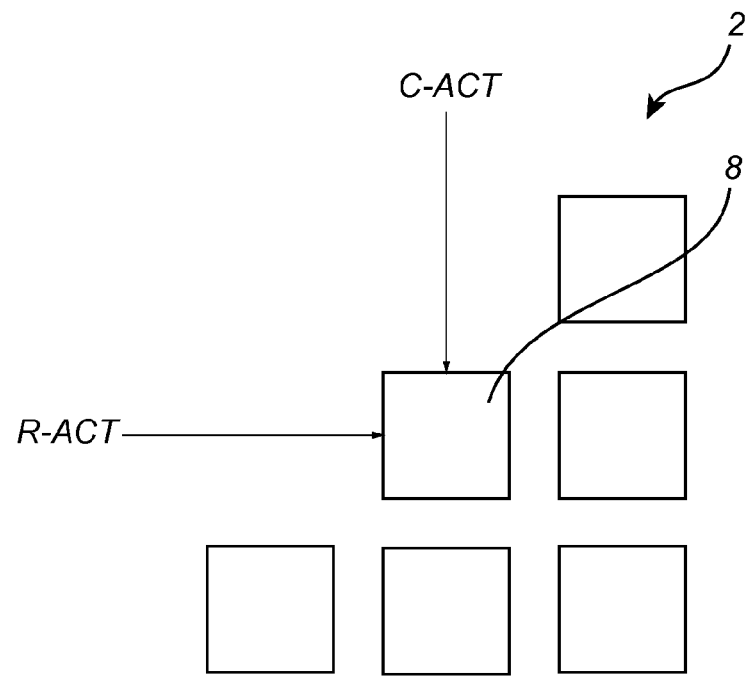
FIG. 5a b schematically illustrate a sensing element comprised in a fingerprint sensing device according to embodiments of the present invention.
Figure 5B:
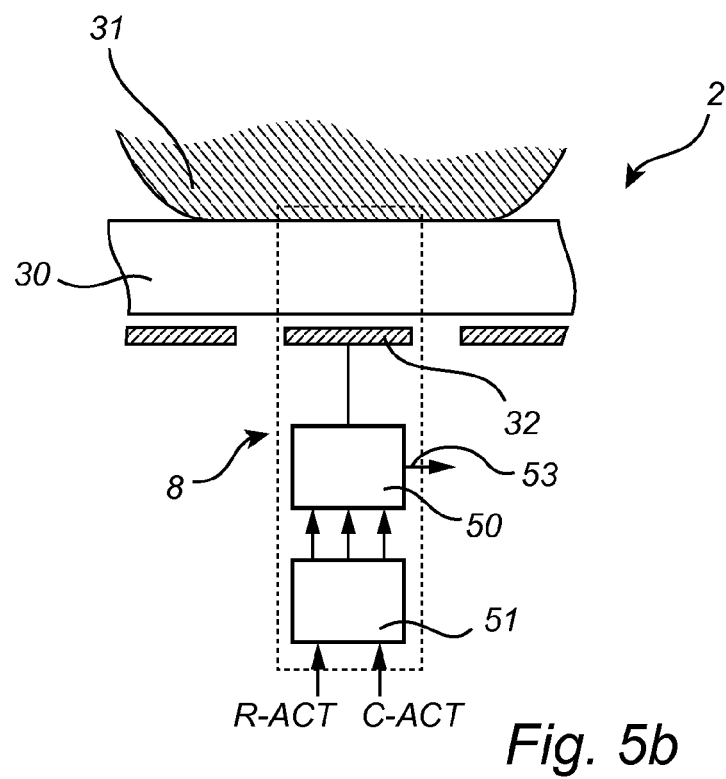

FIG. 5a-b schematically illustrate a sensing element comprised in a capacitive fingerprint sensing device according to embodiments of the present invention.

Referring first to FIG. 5a, a sensing element 8 from the sensor array 5 in FIG. 2 is shown together with its closest neighbors. As was described above with reference to the prior art capacitive fingerprint sensing device 20 in FIG. 3a-c, the sensing element(s) to be sensing the capacitive coupling between its sensing structure and the finger 31 may be selected using activation signals from row selection circuitry and column selection circuitry. Such activation signals are indicated as R-ACT and C-ACT in FIG. 5a. Activation signals like this are also provided to select a particular sensing element 22 in the fingerprint sensing device 20 according to the prior art described above. In that fingerprint sensing device 20 there are, as was also mentioned above, additional timing control signals being routed from the state machine 27 to each sensing element 22. In the fingerprint sensor 20 of FIG. 3a-c, these additional timing control signals, such as the reset signal RST are provided from the state machine 27 to each sensing element to provide central timing control of at least a part of the measurement sequence as described above with reference to FIG. 4.

As will be described below, the capacitive fingerprint sensing device according to embodiments of the present invention, in contrast, provides timing control signals for state transitions in the measurement sequence locally in each sensing element 8 or group of sensing elements. This allows for improved timing control with, for instance, a more uniform and precise timing of control signals, such as the above-mentioned reset control signal RST.

Referring to FIG. 5b, each sensing element 8 in the capacitive fingerprint sensing device 2 comprises charge measuring circuitry 50 and timing circuitry 51.

The charge measuring circuitry 50 is connected to the sensing structure (plate) 32 for measuring the change of the charge carried by the sensing structure 32 resulting from a change in a potential difference between the finger 31 and the sensing structure 32. This measurement is, as was described above with reference to FIG. 4, carried out by performing a measurement sequence comprising transitioning through a sequence of measurement states. The charge measuring circuitry 50 has an output 53 for providing a signal indicative of the change of the charge carried by the sensing structure 32 resulting from a change in potential difference between the potential of the sensing structure 32 and the potential of the finger 31.

The timing circuitry 51 is connected to the charge measuring circuitry 50 for controlling a timing of at least one of the measurement states.

As is schematically illustrated in FIG. 5b, the timing circuitry may receive one or several control signals for triggering a measurement operation of the sensing element 8. For instance, the above-mentioned row and column activation signals R-ACT and C-ACT may be received by the timing circuitry 50, which thereafter may independently provide to the charge measuring circuitry 50 various timing control signals as schematically indicated by the arrows in FIG. 5b.

In the example provided here, and using the measurement state representations $S_0$-$S_9$ from FIG. 4, the timing circuitry 51 comprised in the sensing element 8 thus controls the timing of at least one of the measurement states indicated in FIG. 4.

Through this local control of the timing of at least one of the measurement states comprised in the measurement sequence, the timing of transitions between measurement states can be more precisely and/or uniformly controlled, which allows for shorter times between transitions, which in turn allows for a higher measurement frequency.

An example embodiment of the charge measuring circuitry 50 in FIG. 5b will now be described with reference to FIG. 6a.

Figure 6A:
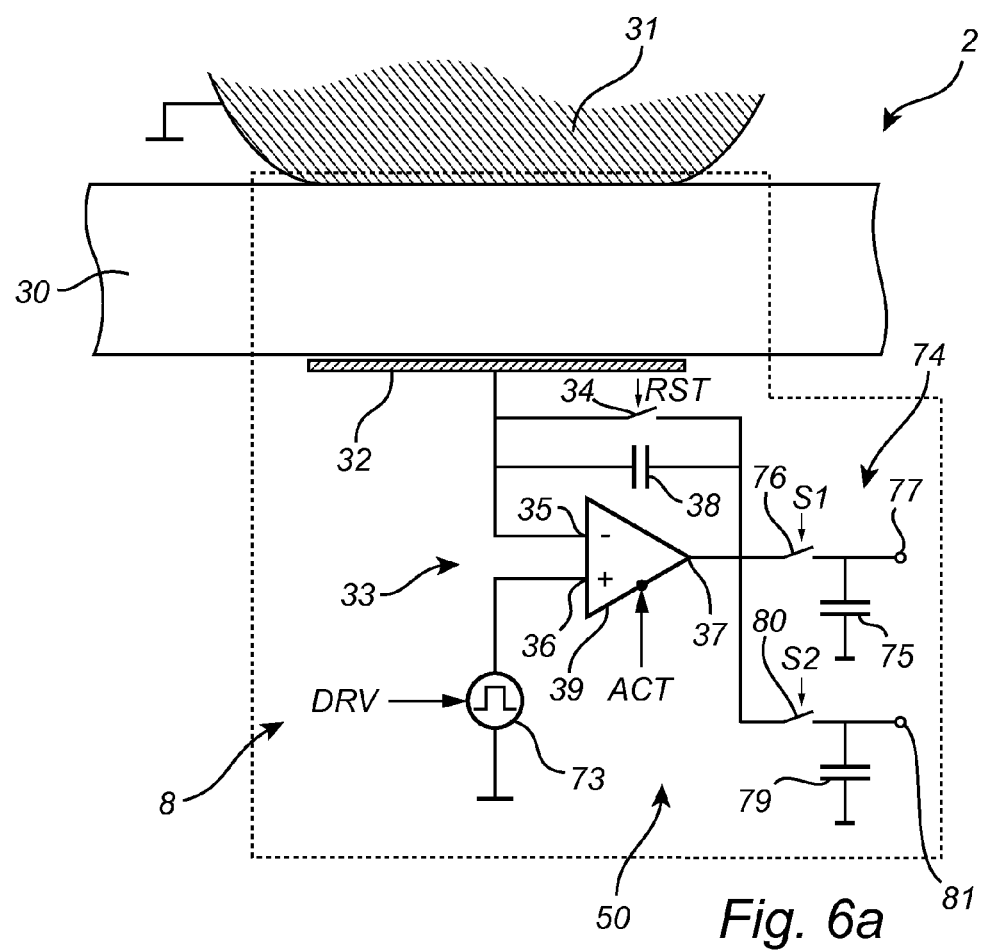
FIG. 6a is a schematic circuit diagram of a part of the sensing element in FIG. 5b, including the charge measuring circuitry.

The charge measuring circuitry 50 in FIG. 6a comprises a charge amplifier 33, excitation signal providing circuitry here represented by a controllable voltage source 73, and sample-and-hold circuitry 74.

As described above for the sensing element 22 in FIG. 3b, the charge amplifier in the charge measuring circuitry 50 of FIG. 6a comprises a negative input 35, a positive input 36, an output 37, a feedback capacitor 38, and an amplifier 39.

The negative input 35 is connected to the sensing structure (plate) 32 and the output 37 is connected to sample-and-hold circuitry 74 comprised in the sensing element 8.

The feedback capacitor 38 is connected between the negative input 35 and the output 37 and defines the amplification of the charge amplifier 33, and the sensing element 22 further comprises a reset switch 34 in parallel with the feedback capacitor 38.

Rather than being directly connected to ground or to another reference potential, the positive input 36 is connected to the controllable voltage source 73.

The sample-and-hold circuitry 74 comprises a first sampling capacitor 75, a first sampling switch 76 and a first output 77, and a second sampling capacitor 79, a second sampling switch 80 and a second output 81.

As is schematically indicated by arrows in FIG. 6a, the charge measuring circuitry 50 can be controlled to perform the measurement sequence described above with reference to FIG. 4 using the above-mentioned control signals (the activation signal ACT, the reset signal RST, the drive control signal DRV, the first sampling control signal S1, and the second sampling control signal S2). When the measurement sequence described with reference to FIG. 4 has been performed, the potential difference between the first 77 and second 81 outputs of the sample-and-hold circuit 74 will be indicative of the capacitive coupling between the sensing structure 32 and the finger 31.

It should be noted that the circuit diagram in FIG. 6a has been simplified to facilitate description of embodiments of the present invention. For instance, level shifting at the output of the sensing element 8 has been omitted. Implementation of level shifting is, however, straight-forward to one of ordinary skill in the art.

Since the charge amplifier is configured in such a way that a potential at the negative input 35 substantially follows a potential at the positive input 36 (so-called virtual ground), the potential at the sensing structure (plate) 32 will substantially follow the time-varying potential, relative to a reference potential of the electronic device comprising the capacitive fingerprint sensing device 2, provided to the positive input 36 through control of the controllable voltage source 73.

Since the potential of the finger 31 is substantially constant in relation to the reference potential of the electronic device (for example through an electrical connection between the electronic device and the hand of the user), the variation over time of the potential at the positive input 36 of the charge amplifier 33 will result in a change in potential difference between the finger 31 and the sensing structure 32, which will in turn result in a change of the charge carried by the sensing structure 32 that is indicative of the capacitive coupling between the finger 31 and the sensing structure (plate) 32.

To facilitate output from the fingerprint sensor 2 of a fingerprint pattern signal indicative of the fingerprint pattern of the finger 31, the voltage $V_{SH}$ between the outputs of the sample-and-hold circuit 74 may be converted to digital form using an analog-to-digital converter, which may be provided outside the sensor array as schematically indicated in FIG. 3a-c.

Figure 6B:
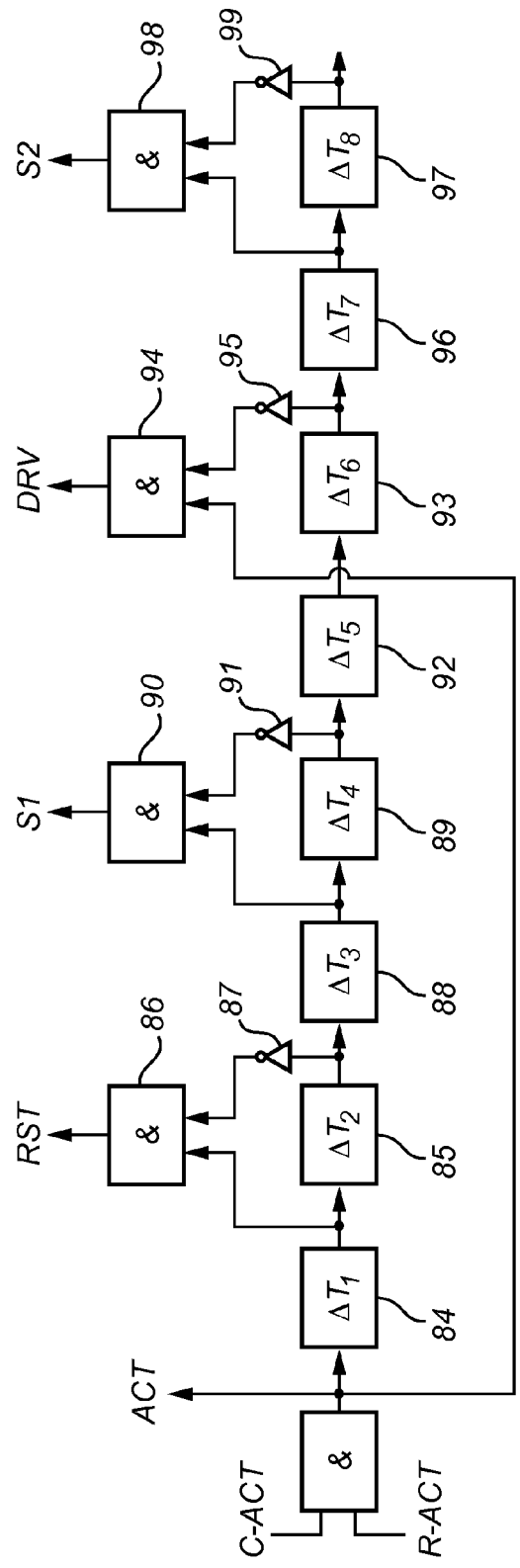

With reference to FIG. 6b, an exemplary configuration of the timing circuit 51 in FIG. 5b will now be described. As can be seen in FIG. 6b, the timing circuit 51 comprises a first AND-gate 83, a first delay element 84, a second delay element 85, a second AND-gate 86, a first inverter 87, a third delay element 88, a fourth delay element 89, a third AND-gate 90, a second inverter 91, a fifth delay element 92, a sixth delay element 93, a fourth AND-gate 94, a third inverter 95, a seventh delay element 96, an eighth delay element 97, a fifth AND-gate 98, and a fourth inverter 99.

As is schematically indicated in FIG. 5l, the row activation signal R-ACT and the column activation signal C-ACT are input to the first logic AND-gate 83. Referring also to FIG. 6a, the output of the first AND-gate 83 is provided to the amplifier 39 of the charge measuring circuitry 50 as the above-mentioned activation signal ACT, to the input of the first delay element 84, and to the fourth AND-gate 94. The output of the first delay element 84 is provided to the second AND-gate 86, and to the input of the second delay element 85. The output of the second delay element 85 is provided to the second AND-gate 86 via the first inverter 87 and to the input of the third delay element 88. The output of the third delay element 88 is provided to the input of the third AND-gate 90 and to the input of the fourth delay element 89. The output of the fourth delay element 89 is provided to the third AND-gate 90 via the second inverter 91, and to the input of the fifth delay element 92. The output of the fifth delay element 92 is provided to the input of the sixth delay element 93. The output of the sixth delay element 93 is provided to the fourth AND-gate 94 via the third inverter 95, and to the input of the seventh delay element 96. The output of the seventh delay element 96 is provided to the input of the eighth delay element 97 and the input of the fifth AND-gate 98. Finally, the output of the eighth delay element 97 is provided to the input of the fifth AND-gate 98 via the fourth inverter 99.

When the sensing element 8 comprising the charge measuring circuitry 50 in FIG. 6a and the timing circuit 51 in FIG. 6b is selected by setting both the row activation signal R-ACT and the column activation signal C-ACT high, the activation signal ACT for the sensing element 8 goes high (at the time $t_1$ with reference to FIG. 4). The output from the first AND-gate 83 passes through the first delay element 84 and is delayed by a first time delay $\Delta T_1$ to provide a first delayed version of the activation signal ACT to the second AND-gate 86.

The first time delay $\Delta T_1$ corresponds to $t_2-t_1$ in FIG. 4 and determines the duration of the first measurement state $S_1$.

The output from the first delay element 84 is also provided to the input of the second delay element 85, and is delayed to provide a second delayed version of the activation signal ACT.

The second delayed version of the activation signal ACT is provided to the input of the second AND-gate 86 via the first inverter 87 to achieve the reset control signal RST on the output of the second AND-gate 86.

The second time delay $\Delta T_2$ corresponds to $t_3-t_2$ in FIG. 4 and determines the duration of the second measurement state $S_2$ (where the reset control signal RST is high).

The remainder of the timing circuit 51 works in the same way, with the delay elements being configured to achieve the control signals shown in the timing diagrams of FIG. 4.

Accordingly, the third time delay $\Delta T_3$ corresponds to $t_4-t_3$ in FIG. 4 and determines the duration of the third measurement state $S_3$, the fourth time delay $\Delta T_4$ corresponds to $t_5-t_4$ in FIG. 4 and determines the duration of the fourth measurement state $S_4$ etc.

It should be noted that the timing circuit 51 is a simplified example for illustrating the principle of using a combination of delay elements and logic gates for locally controlling the timing of measurement states of the charge measuring circuitry comprised in the sensing element. Depending on the actual implementation, the timing circuitry may comprise additional or other circuitry for, for instance, signal shaping and/or timing. Based on the description provided herein, the skilled person will be able to design a suitable implementation of a timing circuit without undue burden.

It should be understood that fewer or additional timing control signals may be independently provided from the timing circuitry 51 to the charge measuring circuitry 50 depending on the particular embodiment.

Figure 7:
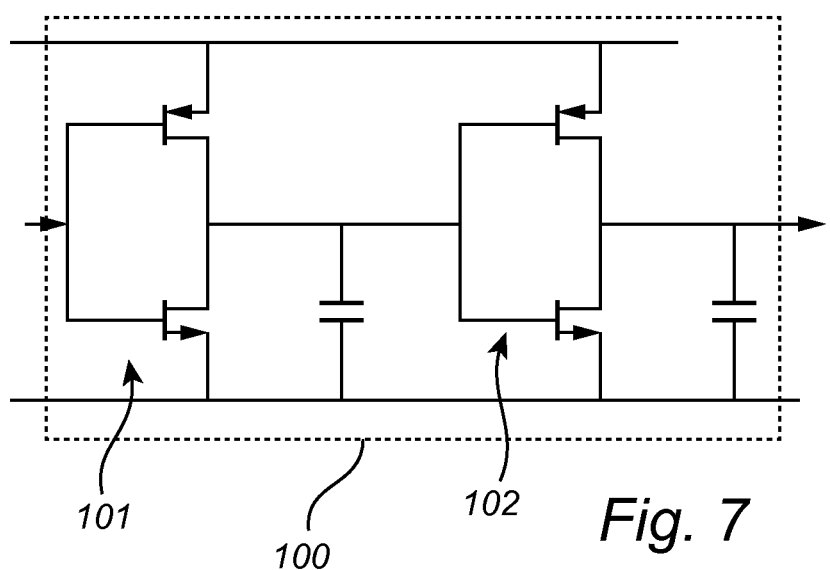
FIG. 7 is a circuit diagram of a delay element comprised in the timing circuit in FIG. 6b.

FIG. 7 shows an illustrative example of a delay element 100 which may be comprised in the timing circuitry 51 in FIG. 6a.

The delay element 100 comprises a first CMOS-inverter 101 and a second CMOS-inverter 102 connected in series. The time delay of this delay element will depend on the dimensioning of the components comprised in the delay element 100, and the time delay can thus be set when designing the delay element. If considerably longer delay times are desired, further CMOS-inverters can be coupled in series.

The person skilled in the art realizes that the present invention by no means is limited to the preferred embodiments described above. On the contrary, many modifications and variations are possible within the scope of the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

What is claimed is:

1. A capacitive fingerprint sensing device for sensing a fingerprint pattern of a finger, said capacitive fingerprint sensing device comprising a plurality of sensing elements, each including:
   a protective dielectric top layer to be touched by said finger;
   an electrically conductive sensing structure arranged underneath said top layer;
   charge measuring circuitry connected to said sensing structure for sequentially transitioning between at least a first measurement state and a second measurement state to perform a measurement sequence resulting in an output signal from said charge measuring circuitry being indicative of a change of a charge carried by said sensing structure resulting from a change in a potential difference between said finger and said sensing structure; and
   timing circuitry connected to said charge measuring circuitry for independently providing at least one timing control signal to said charge measuring circuitry to control a timing of at least one of said measurement states, wherein the timing circuitry comprises at least one delay element.

2. The capacitive fingerprint sensing device according to claim 1, wherein said timing circuitry is configured to control said charge measuring circuitry to transition from said first measurement state to said second measurement state at a transition time defined by a first event and a time delay in relation to said first event.

3. The capacitive fingerprint sensing device according to claim 2, wherein said timing circuitry comprises at least a first delay element having an input for receiving a first signal defining said first event and an output for providing a second signal defining a second event delayed in relation to said first event.

4. The capacitive fingerprint sensing device according to claim 3, wherein said second event comprises said transition from the first measurement state to the second measurement state.

5. The capacitive fingerprint sensing device according to claim 3, wherein the output of said first delay element is coupled to said charge measuring circuitry for allowing said second signal to control operation of said charge measuring circuitry.

6. The capacitive fingerprint sensing device according to claim 3, wherein said timing circuitry further comprises a second delay element having an input coupled to the output of said first delay element and an output for providing a third signal defining a third event delayed in relation to said second event.

7. The capacitive fingerprint sensing device according to claim 6, wherein the output of said second delay element is coupled to said charge measuring circuitry for allowing said third signal to control operation of said charge measuring circuitry.

8. The capacitive fingerprint sensing device according to claim 6, wherein said timing circuitry further comprises at least one logic gate coupled between the output of said first delay element and the input of said second delay element.

9. The capacitive fingerprint sensing device according to claim 3, wherein said timing circuitry comprises a plurality of delay elements each having an input and an output, said delay elements being arranged in a sequence of delay elements in such a way that the output of each of said delay elements is coupled to the input of a next one in said sequence of delay elements.

10. The capacitive fingerprint sensing device according to claim 9, wherein said sequence is a closed loop sequence.

11. The capacitive fingerprint sensing device according to claim 2, wherein, for each of said sensing elements, said first event is provided by an activation signal generated outside said sensing element.

12. The capacitive fingerprint sensing device according to claim 1, wherein said measurement sequence at least comprises:
a reset state in which a potential at an output of said charge measuring circuitry is referenced to a potential of said sensing structure.

13. The capacitive fingerprint sensing device according to claim 1, wherein said charge measuring circuitry comprises a charge amplifier including:
a negative input connected to said sensing structure;
a positive input;
an output;
a feedback capacitor connected between said negative input and said output; and
at least one amplifier stage between said positive and negative inputs, and said output,
wherein said charge amplifier is configured in such a way that a potential at said negative input substantially follows a potential at said positive input.

14. The capacitive fingerprint sensing device according to claim 13, wherein said capacitive fingerprint sensing device further comprises:
excitation signal providing circuitry connected to said positive input and configured to change a potential at said positive input from a first potential to a second potential, to thereby change a potential of said sensing structure, thereby providing said change in potential difference between said finger and said sensing structure.

15. The capacitive fingerprint sensing device according to claim 14, wherein said timing circuitry is connected to said excitation signal providing circuitry for:
providing a first excitation control signal to said excitation signal providing circuitry for triggering said change in potential from the first potential to the second potential at a first excitation transition time; and
providing a second excitation control signal to said excitation signal providing circuitry for triggering a change in potential back from the second potential to the first potential at a second excitation transition time.

16. The capacitive fingerprint sensing device according to claim 1, wherein:
said fingerprint sensing device further comprises excitation signal providing circuitry for providing an excitation signal exhibiting a time-varying excitation potential including recurring changes from a first potential to a second potential and back to the first potential, in relation to a potential of said finger;
each of said sensing elements further comprises demodulation circuitry connected to said charge measuring circuitry for combining said output signal from said charge measuring circuitry and a demodulation signal being timing-related to said excitation signal to provide a combined signal including a DC signal component indicating said change of the charge carried by said sensing structure; and
said fingerprint sensing device further comprises readout circuitry connected to each of said sensing elements for providing a representation of said fingerprint pattern based on said DC signal component from each of said sensing elements.

17. The capacitive fingerprint sensing device according to claim 16, wherein said demodulation circuitry comprises signal multiplication circuitry for multiplying said sensing signal with said demodulation signal.

18. The capacitive fingerprint sensing device according to claim 16, wherein said demodulation circuitry further comprises a low-pass filter for allowing said DC signal component to pass while removing higher frequency components.

19. The capacitive fingerprint sensing device according to claim 1, wherein said charge measuring circuitry comprises sampling circuitry for:
sampling a signal indicative of a charge carried by said sensing structure at a first sampling time before said change in the potential difference between said finger and said sensing structure; and
sampling said signal indicative of the charge carried by said sensing structure at a second sampling time after said change in the potential difference between said finger and said sensing structure.

20. The capacitive fingerprint sensing device according to claim 19, wherein said timing circuitry is connected to said sampling circuitry for:
providing a first sampling control signal to said sampling circuitry for performing said sampling of the first signal at said first sampling time; and
providing a second sampling control signal to said sampling circuitry for performing said sampling of the second signal at said second sampling time.

21. The capacitive fingerprint sensing device according to claim 1, further comprising readout circuitry connected to each of said sensing elements and configured to provide a representation of said fingerprint pattern based on said output signal from each of said sensing elements.

22. An electronic device comprising:
the fingerprint sensing device according to claim 21; and
processing circuitry configured to:
acquire said representation of said fingerprint pattern from the fingerprint sensing device;
authenticate a user based on said representation; and
perform at least one user-requested process only if said user is authenticated based on said representation.

23. A method of sensing a fingerprint pattern of a finger using a capacitive fingerprint sensing device comprising a plurality of sensing elements, each including:
a protective dielectric top layer to be touched by said finger;
an electrically conductive sensing structure arranged underneath said top layer; and
charge measuring circuitry connected to said sensing structure for sequentially transitioning between at least a first measurement state and a second measurement state to perform a measurement sequence resulting in an output signal from said charge measuring circuitry being indicative of a change of a charge carried by said sensing structure resulting from a change in a potential difference between said finger and said sensing structure,
wherein said method comprises the steps of, for each of said sensing elements:
providing a first signal defining a first event;
delaying, in said sensing element utilizing at least one delay element, the first signal for providing a second signal defining a second event delayed in time in relation to the first event; and controlling said charge measuring circuitry to transition from said first measurement state to said second measurement state using said second signal as a control signal.

24. The method according to claim 23, wherein said step of delaying comprises the step of:
passing the first signal through the at least one delay element.

25. The method according to claim 23, wherein said capacitive fingerprint sensing device comprises:
sampling circuitry for sampling said output signal of the charge measuring device;
excitation signal providing circuitry for providing said change in potential difference between said finger and said sensing structure; and
readout circuitry connected to each of said sensing elements and configured to provide a representation of said fingerprint pattern based on said output signal from each of said sensing elements,
wherein said method comprises the steps of:
providing a selection signal for selecting a sensing element;
delaying said selection signal for providing a reset signal;
providing said reset signal to said charge measuring circuitry for transitioning said charge measuring circuitry to a reset state;
delaying said reset signal for providing a measurement ready signal;
providing said measurement ready signal to said charge measuring circuitry for terminating said reset state and transitioning to a measurement ready state;
delaying said measurement ready signal for providing a first sampling control signal;
providing said first sampling control signal to said sampling circuitry for triggering sampling of a first signal indicative of a charge carried by said sensing structure at a first sampling time;
delaying said first sampling control signal for providing a first excitation control signal;
providing said first excitation control signal to said excitation signal providing circuitry for achieving said change in potential difference between said finger and said sensing structure;
delaying said first excitation control signal for providing a second sampling control signal; and
providing said second sampling control signal to said sampling circuitry for triggering sampling of a second signal indicative of a charge carried by said sensing structure at a second sampling time.

* * * * *